US009801536B2

(12) United States Patent
Gandjbakhche et al.

(10) Patent No.: US 9,801,536 B2
(45) Date of Patent: Oct. 31, 2017

(54) POLARIMETRIC ACCESSORY FOR COLPOSCOPE

(71) Applicant: The United States of America, as represented by the Secretary, Department of Health and Human Services, Washington, DC (US)

(72) Inventors: Amir Gandjbakhche, Potomac, MD (US); Victor Chernomordik, Rockville, MD (US); Moinuddin Hassan, Bristow, VA (US); Alexander Sviridov, Moscow (RU); Zachary Ulissi, Bethesda, MD (US); Paul D. Smith, Annapolis, MD (US); Albert C. Boccara, Paris (FR)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 382 days.

(21) Appl. No.: 14/390,354

(22) PCT Filed: Apr. 4, 2013

(86) PCT No.: PCT/US2013/035223
§ 371 (c)(1),
(2) Date: Oct. 2, 2014

(87) PCT Pub. No.: WO2013/152162
PCT Pub. Date: Oct. 10, 2013

(65) Prior Publication Data
US 2015/0112136 A1    Apr. 23, 2015

Related U.S. Application Data

(60) Provisional application No. 61/620,295, filed on Apr. 4, 2012.

(51) Int. Cl.
*A61B 1/303*    (2006.01)
*A61B 1/04*    (2006.01)
(Continued)

(52) U.S. Cl.
CPC ............ *A61B 1/303* (2013.01); *A61B 1/0002* (2013.01); *A61B 1/00009* (2013.01);
(Continued)

(58) Field of Classification Search
CPC ....... A61B 1/303; A61B 1/042; A61B 1/0002; A61B 1/00052; A61B 1/00193; A61B 1/00009; A61B 1/00197; A61B 1/0646
See application file for complete search history.

(56) References Cited

U.S. PATENT DOCUMENTS 7,287,855 B2 * 10/2007 Zhou .................... A61B 3/1005
351/205
8,130,378 B2 * 3/2012 Wu ........................ G01N 21/21
356/364

(Continued)

FOREIGN PATENT DOCUMENTS

JP        2012-024142        2/2012
WO    WO 2009/029254    3/2009

OTHER PUBLICATIONS

A. P. Sviridov, et al. "Compact Polarization Camera with Liquid-Crystal Retarder for Patterning of Biological Textures," Biomedical Optics, OSA Technical Digest (CD) (Optical Society of America, 2008).*

(Continued)

*Primary Examiner* — Kara E Geisel
*Assistant Examiner* — Dominic J Bologna
(74) *Attorney, Agent, or Firm* — Klarquist Sparkman, LLP

(57) ABSTRACT

A polarization-based colposcopy apparatus includes a polarization exchanging beam splitter pair oriented so that s- and p-polarizations are exchanged. An optical flux from a specimen is directed through the pair, and orthogonal components thereof are alternately or selectively coupled to an array detector. The detected images are processed based on image correlations to reveal specimen structures.

21 Claims, 4 Drawing Sheets

(51) Int. Cl.
*A61B 1/00* (2006.01)
*A61B 1/06* (2006.01)

(52) U.S. Cl.
CPC ...... *A61B 1/00052* (2013.01); *A61B 1/00193* (2013.01); *A61B 1/00197* (2013.01); *A61B 1/042* (2013.01); *A61B 1/0646* (2013.01)

(56) References Cited

U.S. PATENT DOCUMENTS

| | | |
|---|---|---|
| 2002/0065468 A1 | 5/2002 | Utzinger et al. |
| 2005/0275848 A1* | 12/2005 | Hill .................... G01B 11/2441 356/512 |
| 2006/0028652 A1 | 2/2006 | Chan et al. |
| 2006/0241495 A1 | 10/2006 | Kurtz |
| 2007/0146632 A1 | 6/2007 | Chipman |
| 2008/0200817 A1 | 8/2008 | De Martino et al. |
| 2009/0292170 A1* | 11/2009 | Boebel ............... A61B 1/00193 600/111 |
| 2010/0026785 A1 | 2/2010 | Soto-Thompson et al. |

OTHER PUBLICATIONS

International Search Report and Written Opinion from International Application No. PCT/US2013/035223, dated Jul. 11, 2013, 8 pages.
Extended European Search Report from European Patent Application No. 13772208.8, dated Oct. 19, 2015, 6 pages.

* cited by examiner

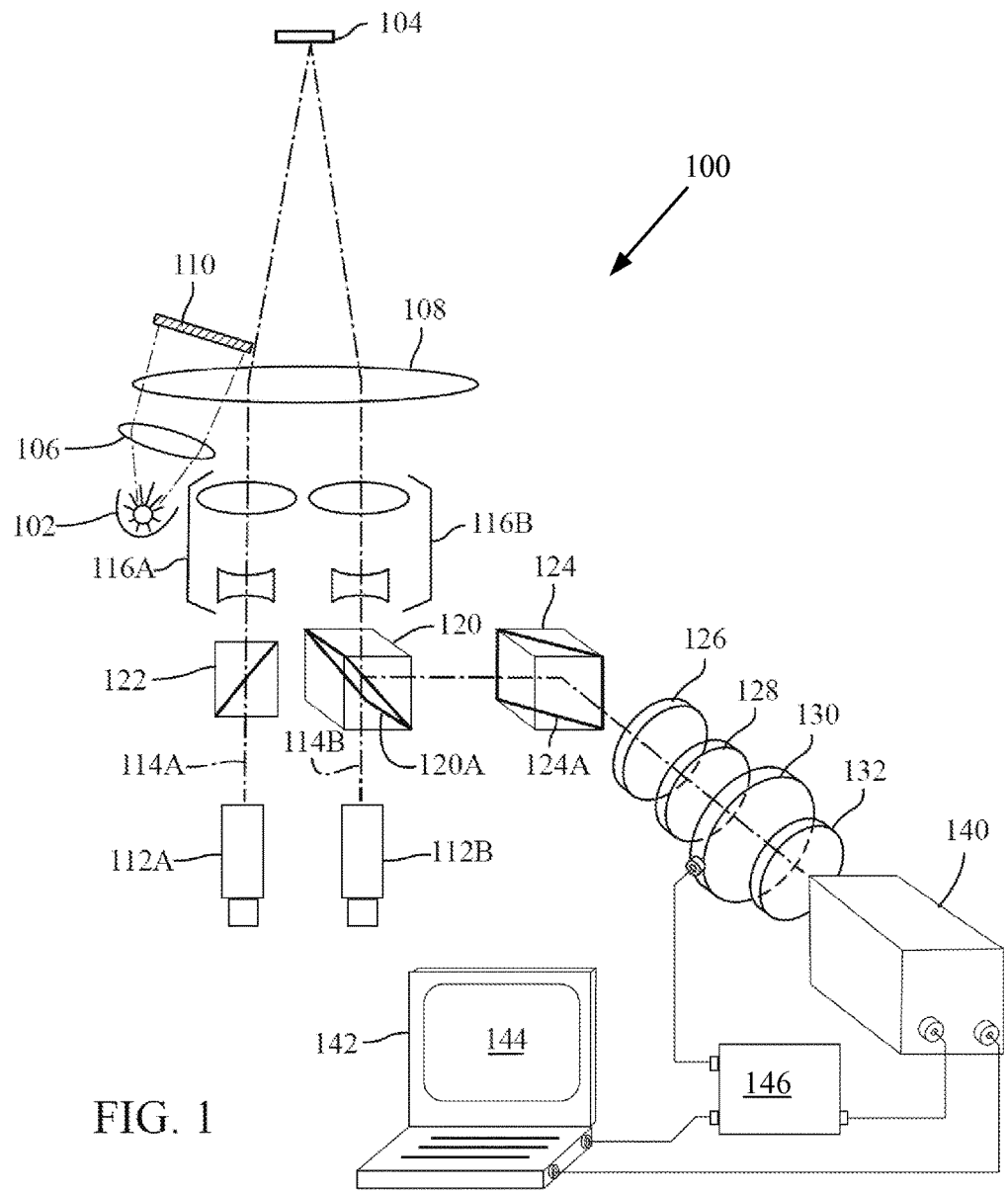
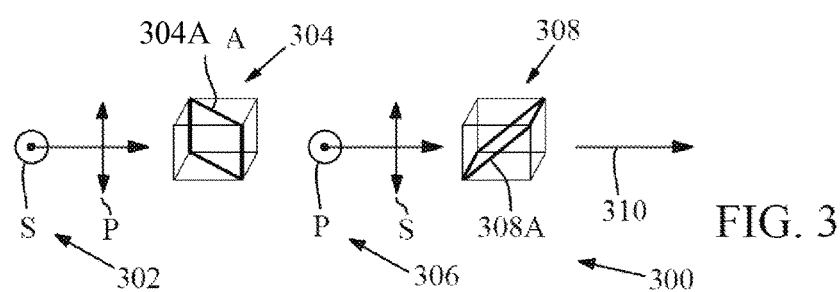
FIG. 1
FIG. 3

POLARIMETRIC ACCESSORY FOR COLPOSCOPE

CROSS REFERENCE TO RELATED APPLICATIONS

This is the U.S. National Stage of International Application No. PCT/US2013/035223, filed Apr. 4, 2013, which was published in English under PCT Article 21(2), which in turn claims the benefit of U.S. Provisional Application No. 61/620,295, filed Apr. 4, 2012, of which is incorporated herein by reference in its entirety.

FIELD OF THE DISCLOSURE

The disclosure pertains to polarization-based colposcopy.

BACKGROUND

Cervical examinations and the assessment of the tissues of the vagina and the vulva are often performed with a binocular microscope configured to have a long working distance (about 30 cm) and a magnification of up to 25. A video or still camera can be provided to recorded images produced by the microscope. Examination based on such images is known as colposcopy and such specially adapted microscope systems are known as colposcopes. Colposcopy is an important technique for the detection of diseases such as cervical cancer. Unfortunately, specular reflections from tissue surfaces can make colposcopic tissue assessments difficult as specular reflections can obscure sub-surface structures.

SUMMARY OF THE DISCLOSURE

In some examples, imaging apparatus comprise a binocular viewing head that defines a first imaging optical path and a second imaging optical path associated with respective eyepiece tubes. A polarization exchanging beam splitter pair (PEBSP), a variable waveplate, and a polarizer are situated in the second optical path and configured to selectively direct specimen imaging fluxes corresponding to a first polarization state and a second polarization state to an imaging optical system associated with the second optical path. In some examples, first and second eyepieces are provided and retained in respective eyepiece tubes. In typical examples, the variable waveplate is a half waveplate that is variable so that the first and second polarization states are linear, orthogonal polarization states. In some embodiments, the imaging optical system includes an array detector configured to receive specimen images associated with the first polarization state and second polarization state, and a memory configured to store the specimen images. In additional examples, an optical attenuator is situated in the first imaging optical path and configured to compensate insertion loss in the second imaging optical path associated with the PEBSP. In some examples, the optical attenuator is configured so that viewable images associated with the first and the second imaging optical paths provide substantially the same intensities. In other embodiments, an image processor is configured to determine a correlation image based on specimen images in the first and second polarization states. In some examples, a display is provided for viewing at least one correlation image. In typical examples, the images are based on a Pearson correlation.

Imaging methods comprise obtaining at least a first specimen image and a second specimen image based on an optical flux received from a PEBSP, wherein the first and second specimen images are associated with different states of polarization from the specimen. The first image and the second image can be used to identify polarization dependent image portions and, in some examples, are used to display an associated image such as a correlation image. In typical examples, the first specimen image and the second specimen image are obtained based on received light fluxes in orthogonal linear states of polarization. In some examples, the imaging optical fluxes are transmitted through a variable retarder and a linear polarizer to an image detector so as to produce selectively detected imaging optical flux portions. In some examples, the variable retarder is selectively varied to produce substantially 0 or ½ wave retardance to produce the selectively detected imaging optical flux portions.

In other examples, apparatus comprise an optical flux source configured to deliver an optical flux to a specimen in a selected state of polarization. An objective lens is configured to form an image of the specimen based on the delivered optical flux. A PEBSP is configured to receive the optical flux, and a variable waveplate is situated to receive the optical flux from the PEBSP and deliver the optical flux to a polarizer. An image sensor is situated to receive the polarized optical flux and an image processor is configured to store associated optical images as corresponding recorded images. In some examples, the polarizer is a linear polarizer, and the variable waveplate has an axis at 45 degrees with respect to the linear polarizer and is switchable to have retardation values of about 0 and about 180 degrees. In other alternatives, the apparatus further comprises a processor configured to produce a correlation image of the specimen based on recorded images associated with at least one of the first and second retardation values of the variable retarder. In typical examples, the first and second retardation values differ by about one half wave. In representative examples, the correlation images are based on a Pearson's correlation.

The foregoing and other features and advantages of the disclosed technology will become more apparent from the following detailed description of a several embodiments which proceeds with reference to the accompanying figures.

BRIEF DESCRIPTION OF THE FIGURES

FIG. 1 is a schematic diagram of a representative apparatus for evaluating biological tissues.

FIG. 3 is a schematic diagram of a portion of an optical system suitable for use in tissue evaluation.

DETAILED DESCRIPTION

Figure 2:
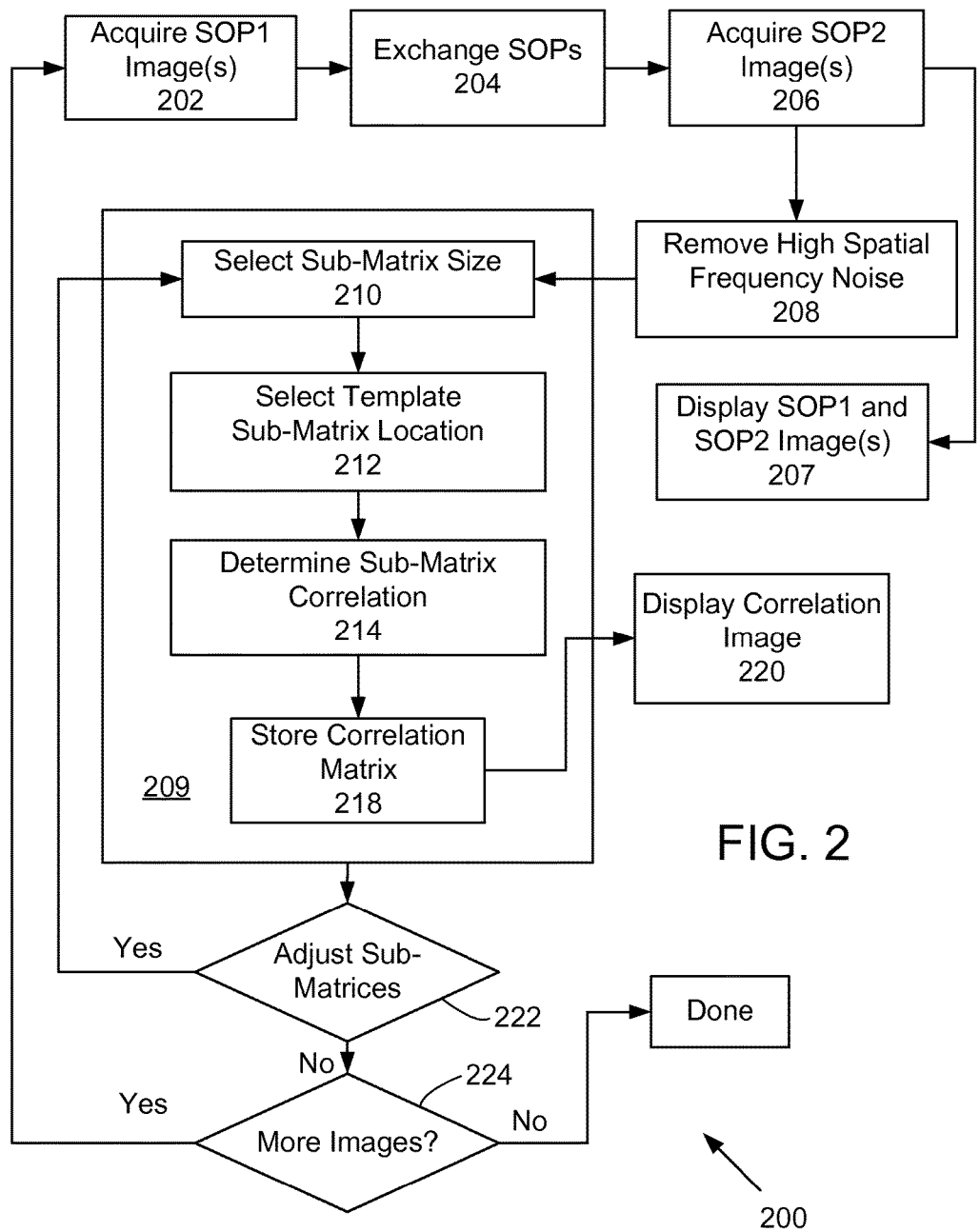
FIG. 2 is a block diagram of a representative method of acquiring and analyzing tissue images.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and subcombinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some disclosed examples, images of specimens under investigation are formed for direct viewing such as images viewable by a user through a microscope eyepiece or projected onto a viewing screen. In addition, data associated with such images can be recorded, typically as digital data in one or more computer readable media such as in random access memory, on a flashdrive or hard disk, or other media. Recorded data can be stored as intensity values for a pixel array for one or more image color components. For example, intensity values for a particular color component can be recorded. In some examples, multiple images can be recorded for a plurality of color components. Recorded images can be stored in a variety of formats, including TIFF, JPEG, and others as may be convenient.

In the following examples, viewable and recorded images are obtained based one or more states of polarization (SOPs) of a light flux received from a specimen. In the disclosed examples, a light flux refers to electromagnetic radiation at wavelengths or frequencies to which the human eye is responsive, generally considered to be between about 400 nm and 700 nm. However, other wavelengths and ranges can be used for specimen evaluation. In some examples, optical radiation at visible or other wavelengths can be used. The disclosed examples are described with reference to linear SOPs, but elliptical or circular SOPs can be used as well. In addition, the disclosed examples are generally directed to specimen evaluation based on images associated with linear SOPs for convenient explanation, but in other examples, other polarization related properties can be used such as degree of polarization, handedness, ellipticity, or any other properties such as those based on one or more or any combination of Stokes parameters associated with optical radiation received from a specimen. The disclosed examples generally are based on refractive optical elements, but reflective elements or combinations of refractive and reflective elements can be used.

In some examples, polarized light based methods in colposcopy can permit rapid, sensitive tissue assessments while reducing the visual impairments associated with specular reflections from tissues. Polarized light based methods can aid in the detection of malignancies without subjecting a patient to harmful or uncomfortable radiation exposures. Laboratory assessments can be similarly useful, as specimen preparation can be simple, and only a visual assessment by a clinician may be needed. However, such techniques can be limited by the introduction of specular reflection artifacts in microscopes or other optical systems. In some cases, specular artifacts may dominate any images so that important tissue characteristics are not apparent. Disclosed herein are methods and apparatus that can permit practical polarized light based tissue assessments such as those required in colposcopy. However, the disclosed methods and apparatus can be used in a variety of applications, and are not limited to colposcopy.

With reference to FIG. 1, an apparatus 100 for polarization based specimen evaluation includes an optical radiation source 102 that is configured to produce a flux that is directed to a specimen 104 via a condenser lens 106, an objective lens 108, and a first polarizer 110. Typically the first polarizer 110 is a linear polarizer having a fixed or variable axis, but in other examples, other polarization components such as variable liquid crystal retarders, or rotatable waveplates can be provided to vary the SOP provided to the specimen 104. As shown in FIG. 1, the apparatus 100 also includes eyepieces 112A, 112B that are situated along axes 114A, 114B, respectively, so as to produce viewable images in conjunction with respective zoom optical systems 116A, 116B and the objective lens 108. Accordingly, some components of the apparatus 100 form a binocular zoom microscope. A first beam splitter 120 is situated along the axis 114B so as to reflect a portion of the optical radiation received from the specimen 104 along a measurement axis 115, and an optical compensator 122 is situated along the axis 114A so as to attenuate optical radiation received along the axis 114A so as to correspond to attenuation introduced by the beam splitter 120. In order to facilitate polarization analysis, the beam splitter 120 is generally a non-polarizing beam splitter having reflectivities $(R_s, R_p)$ and transmittances $(T_s, T_p)$ for an s-polarization and a p-polarization, respectively, such that |Rs−Rp|<0.05, 0.10, 0.20, 0.25, or 0.30 and |Ts−Tp|<0.05, 0.10, 020, 0.25, or 0.30. Beam splitter cubes are convenient, but plate beam splitters, or other optical elements such as holographic or diffractive elements can be similarly arranged.

A second non-polarizing beam splitter 124 is situated along the measurement axis 115 so as to receive the reflected flux from the beam splitter 120, and reflect at least a portion to an imaging lens 126, a bandpass filter 128, a variable retarder (variable waveplate) 130, and a second polarizer 132. A camera 140 is situated so as to receive an image produced by the imaging lens 126, and couple image data to a computer system 142 or other processing system for image analysis based on one or more sets of computer-executable instructions. The computer system 142 includes a display screen 144 for viewing of recorded images or processed images as may be convenient. A waveplate controller 146 is coupled to the variable retarder 130 and the camera 140 so that images can be acquired by the camera 140 as a function of a selected configuration of the variable retarder 130.

While non-polarizing beam splitters such as beam splitters 120, 124 can exhibit low polarization dependence, for some specimen evaluations, even such small polarization dependence can be undesirable. As shown in FIG. 1, the beam splitters 120, 124 include respective reflective surfaces 120A, 124A such that an s-component of a flux that is reflected by the reflective surface 120A is reflected as a p-polarization by the reflective surface 124A. Similarly, a p-component of a flux that is reflected by the reflective surface 120A is reflected as an s-component by the reflective surface 124A. Thus, polarization effects introduced by the beam splitters 120A, 124A can be reduced by using beam splitters having similar or identical properties, typically by using beam splitters made by similar processes, or acquired from a single vendor and having nominally the same characteristics. For convenience, a pair of non-polarizing beam splitters configured so that a first beam splitter reflects an s-component or a p-component and a second beam splitter reflects the p-component or the s-component from the first beam splitter is referred to herein as a polarization exchanging beam splitter pair (PEBSP).

In a typical configuration, the polarizers 110, 132 are linear polarizers arranged so that in the absence of any polarization changes produced by the specimen 104 and the variable waveplate 130, any received flux from the specimen 104 is substantially attenuated, and preferably extinguished. This configuration can be referred to as a crossed-polarizer configuration. The waveplate 130 can be conveniently provided as a liquid crystal waveplate that can be controlled by the waveplate controller 146 to provide half-wave retardation. In addition, a waveplate axis is situated at an angle of about 45 degrees with respect to a polarization axis of the polarizer 132. With this arrangement, a linear polarization component perpendicular to the polarization axis of the polarizer 132 and incident to the waveplate 130 is rotated so as to be along the polarization axis and thus transmitted by the polarizer 132. In this configuration, the polarizers 110, 132 effectively have parallel axes, and this configuration can be referred to as a parallel polarizer or co-polarized configuration. The waveplate 130 generally provides a wavelength dependent retardation, and the bandpass filter 128 selects a suitable wavelength range.

In operation, the variable waveplate 132 is controlled so as to switch between crossed polarizer and parallel polarizer configurations, so that corresponding images can be acquired by the camera 140 and stored at the computer system 142. Images can be periodically selected and displayed on the display 144 or transmitted for remote viewing. In addition, an operator can continue to view the specimen 104 directly. In some examples, the compensator 122 can be a variable compensator so that intensities in the eyepieces 112A, 112B can be matched. In other examples, a second PEBSP can be provided instead of the optical compensator 122 so that co-polarized and cross-polarized images can be produce simultaneously, and an additional camera and imaging lenses can be provided, or additional optics can be provided so that the field of view of the camera 140 is configured to receive the two polarization based images side by side. The recorded images can be evaluated in various ways to provide specimen assessment.

A representative method 200 of processing images such as co-polarized and cross-polarized images is illustrated in FIG. 2. At 202, one or more recorded images associated with a first SOP are received and stored as image matrices $G_1$. Typically, such recorded images are produced with an optical flux from a specimen of interest that is directed to an image sensor through a linear polarizer. At 204, a variable waveplate having an axis at 45 degrees with respect to a transmission axis of the linear polarizer used to acquire the image matrices $G_1$ is controlled to provide one-half wave retardation. At 206, one or more recorded images associated with a second SOP are received and stored as image matrices $G_2$. Using the variable waveplate this manner, the image matrices $G_1$, $G_2$ are associated with orthogonal linear polarizations from the specimen but transmitted by a common polarizer.

In other examples, the images can be obtained by rotating a half wave retarder by 45 degrees or a linear polarizer by 90 degrees. In further examples, SOP1 and SOP2 are linear or elliptical SOPs, and need not be mutually orthogonal. Typically, one or both of the images are viewed or displayed at 207. In some cases, the SOP1 and SOP2 images are alternately superimposed or are displayed side-by-side on a display, or are directly viewed by a clinician. High spatial frequency noise can be filtered from some or all images at 208. At 209, one or more images are processed to reveal specimen structure. At 210, one or more sub-matrix sizes such as m by n are determined, wherein m, n are nonnegative integers. At 212, a particular image location can be selected about which a template sub-matrix can be selected. At 216, a sub-matrix correlation is determined based on sub-matrices A, B which are selected from at least one of the image matrices $G_1$, $G_2$, wherein the matrices A, B are offset by distances $r=[\Delta m, \Delta n]$. Typically, matrixes A, B corresponding to both states of polarization are processed. One of the sub-matrixes A, B is fixed in correlation determinations described below, and can be referred to as the template matrix having a location in the corresponding image as selected at 212. For example, a template sub-matrix $A_1$ can be selected from an image $G_1$ associated with SOP1, and a sub-matrix $B_1$ can be selected from an image $G_1$ associated with the same SOP1. Typically, a location of the template sub-matrix is selected based on a possible region of interest in a specimen, or a particular specimen structure to be investigated throughout a specimen image. An image from the set of images $G_2$ is similarly selected and processed in the same manner.

Correlation can be based on, for example, a Pearson correlation coefficient corr(A, B)(r) that is calculated for a plurality of offsets, wherein corr(A,B) is defined as:

$$\text{corr}(A, B) = \frac{\sum_{k=1}^{m}\sum_{l=1}^{n}(A_{k,l} - \overline{A})(B_{k,l} - \overline{B})}{mn \; stddev(A) stddev(B)},$$

wherein k, l are nonnegative integers, stddev(A), stddev(B) are the standard deviations and $\overline{A},\overline{B}$ are the mean values of the elements the sub-matrices A, B, respectively. The results of the correlation calculation are stored in a memory at 218. Typically, the processed images (i.e., correlation images) are displayed at 220. A different sub-matrix configuration can be selected at 222, and additional images in one or both of SOP1 and SOP2 can be acquired at 224, if desired.

Image processing can be performed with suitable computer-executable instructions on a personal computer or general purpose computer, or a dedicated processor can be provided. Images processed based on the correlation described above generally exhibit little sensitivity to linear transforms such as overall image intensity. In addition, images processed in this manner can permit assessment of the size and orientation of specimen features. In some examples, direct viewing of SOP1, SOP2 images is sufficient and additional image processing can be omitted.

FIG. 3 illustrates a portion 300 of an optical system that is suitable for transmitting optical fluxes from a specimen while preserving flux SOP. A flux 302 is illustrated incident to a beam splitter cube 304 that has a beam splitter surface 304A. The flux 302 can include an s-polarized component that is shown as directed perpendicularly to the plane of FIG. 3, and a p-component that is in the plane of FIG. 3. The s- and p-directions are established by the direction of propagation of the flux 302 and an orientation of the beam splitter surface 304A. The flux 302 (a transmitted portion thereof) propagates as a flux 306 to a cube beam splitter 308. As shown in FIG. 3, the flux 306 can include a p-polarized component that is shown as directed perpendicularly to the plane of FIG. 3, and an s-component that is in the plane of FIG. 3. With this configuration, with matched beam splitters, differences in reflectivity/transmissivity of s- and p-polarizations by the beam splitters 304, 308 are at least partially compensated. In this example, the flux 302 is transmitted by both beam splitters 304, 308, but in other examples, an input flux is reflected by matching beam splitters as shown in FIG. 1.

Figure 4:
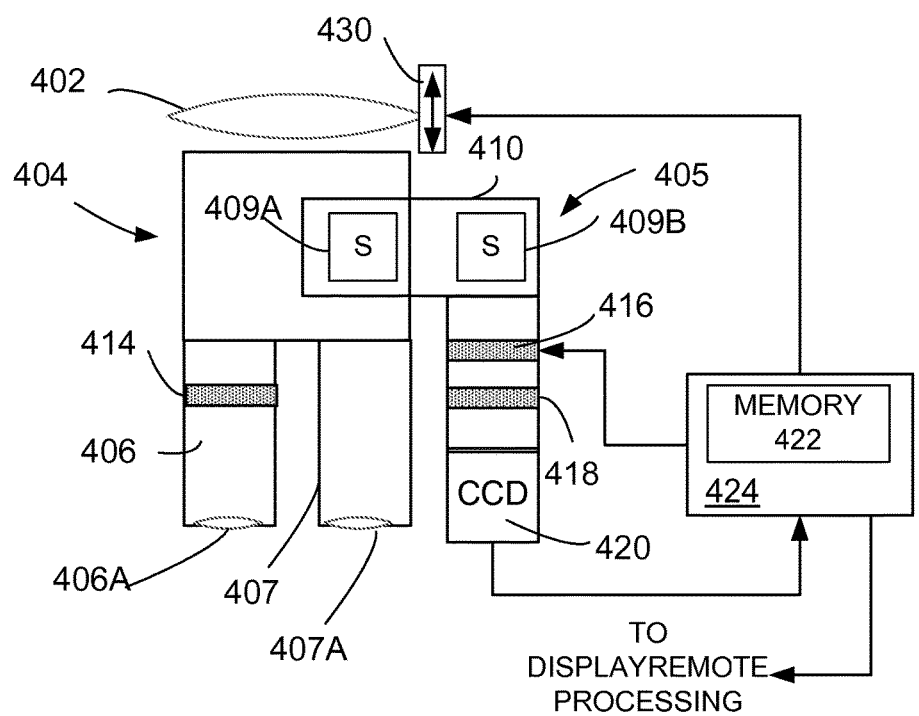
FIG. 4 is a schematic diagram of a portion of an additional embodiment of a colposcope.

With reference to FIG. 4, a colposcope 400 includes one or more objective lenses such as lens 402 configured to form an image of a specimen. The lens 402 is coupled to a binocular microscope head 404 that includes eyepiece tubes 406, 407 configured to retain respective eyepiece lenses 406A, 407A. The binocular head 404 is configured to retain a polarization analysis module 405 so as to divert a portion of an optical flux propagating to the eyepiece tube 407A. The module 405 includes beam splitters 409A, 409B that are configured so that an s-polarization input to the beam splitter 409A would be a p-polarization at the beam splitter 409B. Similarly, the beam splitters 409A, 409B are configured so that a p-polarization input to the beam splitter 409A would be an s-polarization at the beam splitter 409B. The beam splitters 409A, 409B are nominally polarization insensitive plate or cube beam splitters, but typically exhibit some polarization dependence that can interfere with specimen analysis absent the polarization exchanging arrangement illustrated.

The module 405 also includes a variable retarder 416 and a polarizer 418. The variable retarder 416 is conveniently a linear retarder that is switchable from 0 to ½ wave retardation. If the polarizer 418 is a linear polarizer, an axis of the variable retarder 416 is set to be about 45 degrees from the polarization axis of the linear polarizer 418. The variable retarder 416 is thus situated so as to selectively transmit orthogonally polarized portions of an imaging light flux. A CCD 420 or other array detector is situated to receive images based on the selected polarization, and a controller 424 includes a memory 422 for image storage. Images can be processed at the controller 424, and coupled to a display, or the image data can be communicated by a wired or wireless network for evaluation and viewing at a remote or local location.

In many examples, visible radiation is used for imaging so that images are directly viewable by a clinician. Because insertion of the beam splitter 409A in the optical path associated with the eyepiece tube 407 tends to reduce image intensity, a neutral density filter 414 can be situated in an optical path associated with the eyepiece tube 406 so that the images are more balanced in intensity. In some examples, infrared radiation can be used for polarization analysis to better image below a tissue surface, and viewable visible images can be provided while infrared radiation is directed to the detector 420. In this case, the beam splitters 409A, 409B can be configured to transmit visible radiation. Is some cases (with or without different viewing and polarization analysis wavelengths), a focus adjuster 430 can be coupled to the controller 424 so that images at various distances above and below a specimen surface can be acquired, if desired. It can be advantageous to image below a specimen surface. For example, a skin surface can obscure structural details under investigation that are situated beneath the skin surface. The controller 424 can vary focal depth while controlling the variable retarder 416 so that images associated with orthogonal polarizations can be obtained at a plurality of depths.

Typically, the transmission axis of the polarizer 418 is aligned so to correspond to an s- or p-polarization direction at the beam splitter 409B, but other orientations can be used. For convenience, FIG. 4 does not show other optical component such as narrow band or pass band filters, additional imaging elements for imaging at the array detector 418. In addition, an illumination source is not shown, although usually provided so as to direct a polarized optical flux to the specimen.

Figure 5:
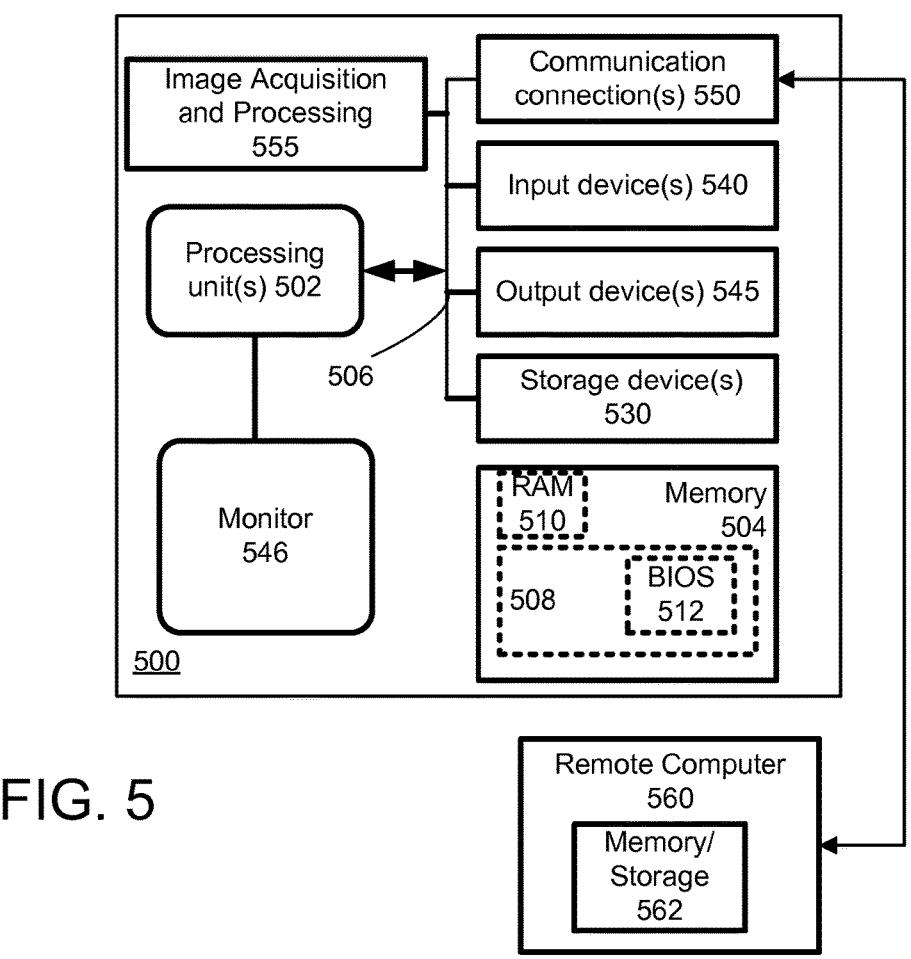
FIG. 5 is schematic diagram of a representative computing environment for image processing, storage, and communication.

FIG. 5 and the following discussion are intended to provide a brief, general description of an exemplary computing environment in which the disclosed technology may be implemented. For example, images acquired as shown above can be processed and displayed. Although not required, the disclosed technology is described in the general context of computer-executable instructions, such as program modules, being executed by a personal computer (PC). Generally, program modules include routines, programs, objects, components, data structures, etc., that perform particular tasks or implement particular abstract data types. Moreover, the disclosed technology may be implemented with other computer system configurations, including hand-held devices, multiprocessor systems, microprocessor-based or programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices.

With reference to FIG. 5, an exemplary system for implementing the disclosed technology includes a general purpose computing device in the form of an exemplary conventional PC 500, including one or more processing units 502, a system memory 504, and a system bus 506 that couples various system components including the system memory 504 to the one or more processing units 502. The system bus 506 may be any of several types of bus structures including a memory bus or memory controller, a peripheral bus, and a local bus using any of a variety of bus architectures. The exemplary system memory 504 includes read only memory (ROM) 508 and random access memory (RAM) 510. A basic input/output system (BIOS) 512, containing the basic routines that help with the transfer of information between elements within the PC 500, is stored in ROM 508.

The exemplary PC 500 further includes one or more storage devices 530 such as a hard disk drive for reading from and writing to a hard disk, a magnetic disk drive for reading from or writing to a removable magnetic disk, and an optical disk drive for reading from or writing to a removable optical disk (such as a CD-ROM or other optical media). Such storage devices can be connected to the system bus 506 by a hard disk drive interface, a magnetic disk drive interface, and an optical drive interface, respectively. The drives and their associated computer-readable media provide nonvolatile storage of computer-readable instructions, data structures, program modules, and other data for the PC 500. Other types of computer-readable media which can store data that is accessible by a PC, such as magnetic cassettes, flash memory cards, digital video disks, CDs, DVDs, RAMs, ROMs, and the like, may also be used in the exemplary operating environment. In some cases, a separate storage device 555 can be provided for storage of computer-executable instructions for image acquisition and control.

A number of program modules may be stored in the storage devices 530 including an operating system, one or more application programs, other program modules, and program data. A user may enter commands and information into the PC 500 through one or more input devices 540 such as a keyboard and a pointing device such as a mouse. Other input devices may include a digital camera, microphone, joystick, game pad, satellite dish, scanner, or the like. These and other input devices are often connected to the one or more processing units 502 through a serial port interface that is coupled to the system bus 506, but may be connected by other interfaces such as a parallel port, game port, or universal serial bus (USB). A monitor 546 or other type of display device is also connected to the system bus 506 via an interface, such as a video adapter. Other peripheral output devices, such as speakers and printers (not shown), may be included.

The PC 500 may operate in a networked environment using logical connections to one or more remote computers, such as a remote computer 560. In some examples, one or more network or communication connections 550 are included. The remote computer 560 may be another PC, a server, a router, a network PC, or a peer device or other common network node, and typically includes many or all of the elements described above relative to the PC 500, although only a memory storage device 562 has been illustrated in FIG. 5. The personal computer 500 and/or the remote computer 560 can be connected to a logical a local area network (LAN) and a wide area network (WAN). Such networking environments are commonplace in offices, enterprise-wide computer networks, intranets, and the Internet.

When used in a LAN networking environment, the PC 500 is connected to the LAN through a network interface. When used in a WAN networking environment, the PC 500 typically includes a modem or other means for establishing communications over the WAN, such as the Internet. In a networked environment, program modules depicted relative to the personal computer 500, or portions thereof, may be stored in the remote memory storage device or other locations on the LAN or WAN. The network connections shown are exemplary, and other means of establishing a communications link between the computers may be used.

The methods and apparatus described above can be applied to the assessment of a variety of specimens in applications other than colposcopy. For example, teeth and skin include structures that can be evaluated. For example, skin can exhibit fibrosis after radiation therapy, and this fibrosis can be detected as described above so that suitable therapy can be timely initiated.

In view of the many possible embodiments to which the principles of the disclosure may be applied, it should be recognized that the illustrated embodiments are examples only and should not be taken as a limitation on the scope of the invention. For instance, various components of systems described herein may be combined in function and use. We claim as our invention all subject matter that comes within the scope and spirit of these claims. Alternatives specifically addressed in these sections are merely exemplary and do not constitute all possible alternatives to the embodiments described herein.

We claim:

1. An apparatus, comprising:
   a binocular viewing head that defines a first imaging optical path and a second imaging optical path; and
   a polarization exchanging beam splitter pair (PEBSP), the PEBSP including a pair of non-polarizing beam splitters configured so that a first non-polarizing beam splitter is situated to reflect an s-component or a p-component of an incident optical flux and a second non-polarizing beam splitter situated to reflect the s-component and the p-component of the reflected incident optical flux at the first non-polarizing beam splitter as a p-component or an s-component, respectively, at the second non-polarizing beam splitter,
   a variable waveplate, and a polarizer situated in the second optical path and configured to selectively direct specimen imaging fluxes corresponding to a first polarization state and a second polarization state to an imaging optical system associated with the second optical path.

2. The apparatus of claim 1, further comprising a first eyepiece and a second eyepiece situated on the first and second imaging optical paths, respectively, and configured to produce a viewable binocular image.

3. The apparatus of claim 1, wherein the variable waveplate is a half waveplate that is variable so that the first and second polarization states are linear, orthogonal polarization states.

4. The apparatus of claim 3, wherein the imaging optical system includes an array detector configured to receive specimen images associated with the first polarization state and second polarization state.

5. The apparatus of claim 4, further comprising an image processor configured to store the specimen images in a memory.

6. The apparatus of claim 2, further comprising an optical attenuator situated in the first imaging optical path and configured to compensate insertion loss in the second imaging optical path associated with the PEBSP.

7. The apparatus of claim 6, wherein the optical attenuator is configured so that that viewable images associated with the first imaging optical path and the second imaging optical path have substantially the same intensity.

8. The apparatus of claim 5, further comprising an image processor configured to produce a correlation image based on specimen images associated with at least one of the first and second states of polarization.

9. A method, comprising:
   obtaining at least a first specimen image and a second specimen image based on an optical flux received from an image through a polarization exchanging beam splitter pair (PEBSP), the PEBSP including a pair of non-polarizing beam splitters configured so that a first non-polarizing beam splitter is situated to reflect an s-component or a p-component of the optical flux and a second non-polarizing beam splitter is situated to reflect the s-component and the p-component of the reflected optical flux at the first non-polarizing beam splitter as a p-component or an s-component, respectively, at the second non-polarizing beam splitter, wherein the first and second specimen images are associated with different states of polarization; and
   processing the first image and the second image to identify polarization dependent image portions and produce an associated polarization based images.

10. The method of claim 9, further comprising displaying at least one of the polarization based images.

11. The method of claim 9, wherein the first specimen image and the second specimen image are associated with orthogonal linear states of polarization.

12. The method of claim 11, further comprising selectively detecting imaging optical flux portions associated with the orthogonal linear states of polarization to produce the specimen images.

13. The method of claim 12, further comprising transmitting the imaging optical flux through a variable retarder and a linear polarizer to an image detector so as to produce the selectively detected imaging optical flux portions.

14. The method of claim 13, wherein the variable retarder is selectively varied to produce substantially 0 or ½ wave retardance to produce the selectively detected imaging optical flux portions.

15. An apparatus, comprising:

an optical flux source configured to deliver an optical flux to a specimen in a selected state of polarization;

an objective lens configured to form an image of the specimen based on the delivered optical flux;

a polarization exchanging beam splitter pair (PEBSP) configured to receive the optical flux, the PEBSP including a pair of non-polarizing beam splitters configured so that a first non-polarizing beam splitter is situated to reflect an s-component or a p-component of the optical flux and a second non-polarizing beam splitter is situated to reflect the s-component and the p-component of the reflected optical flux at the first non-polarizing beam splitter as a p-component or an s-component, respectively, at the second non-polarizing beam splitter;

a variable waveplate situated to receive the optical flux from the PEBSP and deliver the optical flux to a polarizer;

an image sensor situated to receive the image; and an image processor configured to stores the received image as a recorded image.

16. The apparatus of claim 15, wherein the polarizer is a linear polarizer.

17. The apparatus of claim 15, wherein the variable waveplate has an axis at 45 degrees with respect to the linear polarizer and is switchable to have retardation values of about 0 and about 180 degrees.

18. The apparatus of claim 15, further comprising a processor configured to produce a correlation image of the specimen based on recorded images associated with at least one of the first and second retardation values of the variable retarder.

19. The apparatus of claim 18, wherein the processor is configured to produce a correlation image of the specimen based on recorded images associated with the first and second retardation values of the variable retarder.

20. The apparatus of claim 18, wherein the first and second retardation values differ by about one half wave.

21. The apparatus of claim 18, wherein the correlation image is based on a Pearson's correlation analysis.

* * * * *